(12) United States Patent
Fine

(10) Patent No.: US 10,684,278 B1
(45) Date of Patent: Jun. 16, 2020

(54) BEAD-BASED ANALYSIS OF A SAMPLE

(71) Applicant: Alentic Microscience Inc., Halifax (CA)

(72) Inventor: Alan Marc Fine, Prospect (CA)

(73) Assignee: Alentic Microscience Inc., Halifax NS ( * ) Notice: Subject to any disclaimer, the term of this patent is extended or adjusted under 35 U.S.C. 154(b) by 0 days.

(21) Appl. No.: 16/368,707

(22) Filed: Mar. 28, 2019

(51) Int. Cl.
*G01N 21/77* (2006.01)
*G01N 33/543* (2006.01)
*G01N 33/50* (2006.01)
*G01N 33/53* (2006.01)

(52) U.S. Cl.
CPC ....... *G01N 33/54313* (2013.01); *G01N 21/77* (2013.01); *G01N 33/5094* (2013.01); *G01N 33/5302* (2013.01); *G01N 33/543* (2013.01)

(58) Field of Classification Search
CPC ......... G01N 33/54313; G01N 33/5094; G01N 21/77; G01N 33/5302; G01N 33/543
See application file for complete search history.

(56) References Cited

U.S. PATENT DOCUMENTS

2006/0216696 A1\* 9/2006 Goguen ........... G01N 33/54326
435/5
2017/0074870 A1\* 3/2017 Konry .................. B01F 5/0647

OTHER PUBLICATIONS

Appelblom, Heidi, et al., "Homogeneous TR-FRET High-Throughout Screening Assay for Calcium-Dependent Multimerization of Sorcin", www.sbsonline.org, Society for Biomolecular Sciences, 2007 (7 pages).
Bidinosti, Michael, et al., "Novel One-Step Immunoassays to Quantify α-Synuclein: Applications for Biomarker Development and High-Throughput Screening", The Journal of Biological Chemistry vol. 287, No. 40, pp. 33691-33705, Sep. 28, 2012 (16 pages).
Kattke, Michele D., et al., "FRET-Based Quantum Dot Immunoassay for Rapid and Sensitive Detection of Aspergillus amstelodami", Sensors 2011 (15 pages).
Medintz, Igor L., et al., "Self-assesmbled nanoscale biosensors based on quantum dot FRET donors", Nature Materials, Oct. 2003 (10 pages).
Shi, Jingyu, et al., "Nanoparticle based fluorescence resonance energy transfer (FRET) for biosensing applications", Journal of Materials Chemistry B, Royal Society of Chemistry, 2015 (17 pages).
Tagit, Oya, et al., "Fluorescence Sensing of Circulating Diagnostic Biomarkers Using Molecular Probes and Nanoparticles", ACS Sensors, pubs.acs.org/acssensors, Oct. 25, 2017 (16 pages).
Zeng, Qinghui, et al., "Constructions of Silver Triangular Nanoplates-Quantum Dots FRET Systems", Scientific Reports, www.nature.com/scientificsreports, May 20, 2016 (8 pages).
Chavda et al., "A Bead Aggregation Assay for Detection of Low-Affinity Protein-Protein Interactions Reveals Interactions between N-Terminal Domains of Inositol 1,4,5-Trosphosphate Receptors", PLOS/One, Mar. 2013, 7 pages.

\* cited by examiner

*Primary Examiner* — Gailene Gabel
(74) *Attorney, Agent, or Firm* — Fish & Richardson P.C.

(57) ABSTRACT

Among other things, two or more different antibodies are caused to bind to one or more units of a chemical component in a sample. Each of the antibodies is attached to one or more beads (e.g., microbeads). The sample is situated on a surface of an image sensor. At the image sensor, light is received originating at a light source that is other than the beads. The received light includes light reflected by, refracted by, or transmitted through the beads. The image sensor captures one or more images of the sample including the beads. At least one of the images of the sample is processed to separately enumerate individual beads and complexes of two or more of the beads attached to the two or more antibodies that are bound to a unit of the chemical component. The results of the processing are used to identify a presence or a level of the chemical component in the sample.

23 Claims, 5 Drawing Sheets

BEAD-BASED ANALYSIS OF A SAMPLE

BACKGROUND

This description relates to bead-based analysis of a sample.

To obtain all the useful information in a sample of whole blood of a patient for purposes of diagnosis, for example, requires not only a complete blood count (CBC) of the various types of blood cells in the blood sample and their hemoglobin content but also a chemical analysis of other components in the acellular portion of blood (e.g., the plasma). Such other components can include molecules and ions of various kinds.

Traditionally, both a CBC and a chemical analysis of blood are performed in a lab on large expensive machines using tubes of venous blood obtained by phlebotomy. Hours or days may be required for the chemical analysis to be completed and the results returned.

SUMMARY

In general, in an aspect, two or more different antibodies are caused to bind to each unit of one or more units of a chemical component in a sample. Each of the antibodies is attached to one or more beads (e.g., microbeads). The sample is situated on a surface of an image sensor. At the image sensor, light is received originating at a light source that is other than the beads. The received light includes light reflected by, refracted by, or transmitted through the beads. The image sensor captures one or more images of the sample including the beads. At least one of the images of the sample is processed to separately enumerate individual beads and complexes of two or more of the beads attached to the two or more antibodies that are bound to each unit of the chemical component. The results of the processing are used to identify a presence or a level of the chemical component in the sample.

Implementations may include one or a combination of two or more of the following features. The two or more different antibodies bind at different locations of a unit of the chemical component. In some cases, the beads attached to at least two of the different antibodies have the same reflective, refractive, and transmissive characteristics. In some cases, the beads attached to at least two of the different antibodies have different reflective, refractive, or transmissive characteristics or combinations of them for the light originating at the light source. The different reflective, refractive, or transmissive characteristics include colors of the beads. The different reflective, refractive, or transmissive characteristics include sizes of the beads. The different reflective, refractive, or transmissive characteristics include shapes of the beads. The different reflective, refractive, or transmissive characteristics include birefringence of the beads. The situating of the sample on the surface of the image sensor includes forming a monolayer of the sample on the surface. The processing includes determining the amount of the chemical component in the sample based on a comparison of (a) the determined relationship between the number of the individual beads and the number of the complexes of beads and (b) known relationships between the number of the individual beads and the number of the complexes of beads in other samples having known amounts of the component. The sample includes whole blood of a human or animal. At least one of the images is processed to determine counts of one or more types of blood cells in the sample. At least one of the images is processed to determine a complete blood count of the sample. The method is done at a point-of-care.

In general, in an aspect, an image sensor has an array of light sensitive elements exposed at a surface of the image sensor. The surface is configured to receive a sample containing units of a chemical component. At least one of the units of the chemical component has two or more different antibodies bound to it. Each of the different antibodies is attached to a single type of bead having the same reflective, refractive, and transmissive characteristics. A light source it is configured to illuminate the sample. The light sensitive elements are configured to receive light from the light source including light reflected by, refracted by, or transmitted through the beads. A processor is configured to (a) receive one or more images captured by the image sensor of the sample including the direct indicator beads based on the received light, (b) process at least one of the images to identify individual beads and complexes of two or more of the beads attached to the two or more antibodies that are bound to the unit of the chemical component, and (c) use information representing the identifying of the individual beads and complexes of two or more beads to determine a presence or an amount or both of the chemical component in the sample.

In general, in an aspect, two or more different antibodies are caused to bind to one or more units of a chemical component in a sample. One or more of the antibodies is attached to one or more beads. At least another of the antibodies is attached at a location on a surface. The sample is applied on a surface of an image sensor, at the image sensor. Light is received originating at a light source and reflected by, refracted by, or transmitted through the one or more beads attached to the antibody. The image sensor captures one or more images of the sample including the one or more beads. At least one of the images of the sample including the one or more beads is processed to identify the location at which the antibody is attached on the surface, and the location is used to determine a presence or a level of the chemical component in the sample.

Implementations may include one or a combination of two or more of the following features. The surface to which the antibodies are attached includes a surface of the image sensor. The surface to which the antibodies are attached includes a surface facing the surface of the image sensor.

In general, in an aspect, an array of light sensitive elements is exposed at a surface of an image sensor. The surface is configured to receive a sample containing one or more units of a chemical component. At least one of the one or more units of the chemical component has bound to it two or more different antibodies. At least one of the antibodies is coupled to one or more beads. At least another of the antibodies is attached at a location on a surface. A light source is configured to illuminate the sample. The light sensitive elements are configured to receive the light originating at the source and reflected by, refracted by, or transmitted through the one or more beads. A processor is configured to (a) receive one or more images captured by the image sensor based on the received light, (b) process at least one of the one or more images to identify the location at which the bead-coupled antibody is attached to the surface, and (c) use the location to determine a presence or a level of the chemical component in the sample.

In general, in an aspect, visible identifying markers are associated with units of chemical components of a sample. One or more images of the sample including the visible identifying markers are captured when the sample is in contact with a surface of an image sensor at which an array of light sensitive elements are exposed. The presence or the level of one or more of the types of chemical components is determined based on the captured images.

In general, in an aspect, a sample includes units of types of chemical components of a sample and visible identifying markers associated with the units. An array of light sensitive elements is exposed at a surface of an image sensor. The image sensor is configured to capture one or more images of the sample including the visible identifying markers when the sample is situated at the surface. A processor is configured to determine the presence or the level of one or more of the chemical components based on the captured images.

In general, in an aspect, both a complete blood count and a chemical analysis are performed of a sample of whole blood on the surface of an image sensor at which an array of light sensitive elements are exposed. The complete blood count and the chemical analysis are based on light originating at a light source other than the sample and reflected from, refracted by, or transmitted by the sample to the surface of the image sensor.

In general, in an aspect, an array of light sensitive elements is exposed at a surface of the image sensor. The surface is configured to receive a sample of whole blood. A light source is configured to illuminate the sample. The light sensitive elements are configured to receive light originating from the source and reflected by, refracted by, or transmitted through the sample. A processor is configured to perform both a complete blood count and a chemical analysis of the sample of whole blood based on light originating at the light source and reflected by, refracted by, or transmitted through the sample to the surface of the image sensor.

These and other aspects, features, implementations, and advantages (1) can be expressed as methods, apparatus, systems, components, program products, business methods, means or steps for performing functions, and in other ways, and (2) will become apparent from the following description and from the claims.

DETAILED DESCRIPTION

Figure 1:
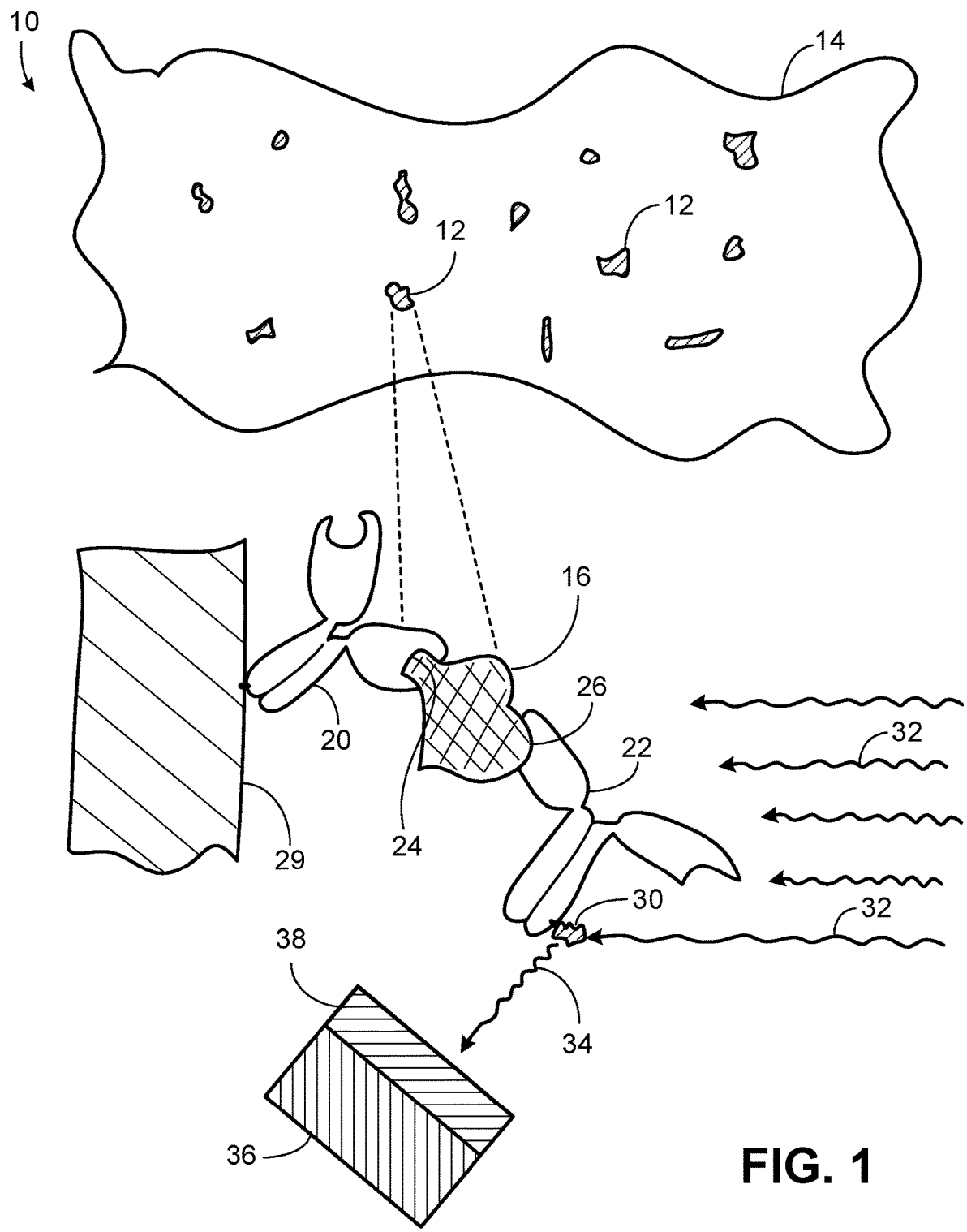
FIG. 1 is a schematic view of a sample.

Here we describe a sample analysis technology that in some implementations can perform a chemical analysis of a sample of whole blood alone or in combination with a CBC directly at a point of care within a few minutes at low cost using a small portable easy-to-use, relatively inexpensive sample analysis device. In some uses, because of its small size and low cost, the sample analysis device can be reproduced in large numbers and distributed to many locations within one or more healthcare, residential, industrial, or commercial locations. In some applications, many units of the sample analysis device can be distributed and used in the field including at locations where equipment for sample analysis (for example, blood chemistry or CBC) is otherwise unavailable or prohibitively expensive.

We use the term "point-of-care" broadly to include, for example, any location in close physical proximity to a patient or other person to whom healthcare is being provided. In many cases, point-of-care refers to services provided in the physical presence of a patient, for example, in the same room or building or at the same place or within a short distance.

Although much of the discussion below refers to applications of the sample analysis technology to chemical analysis of whole blood drawn from a human or other animal, the sample analysis technology can also be applied to a wide range of contexts in which a sample (which may, but need not, be a biological sample) contains chemical components of interest (such as molecules or ions) and that may not involve counting and may or may not include particles, units, or other elements of one or more kinds that are to be counted.

We use the term "sample" broadly to include, for example, any fluid or other mass or body of material that contains one or more analyzable chemical components and may or may not also contain one or more countable units of one or more types. The countable units may in some cases be opaque, translucent, or otherwise non-transparent to incident light. The analyzable chemical components may in some instances be transparent, translucent, or otherwise non-opaque to incident light. In some examples, the sample is whole blood containing countable blood cells of different types and also containing analyzable chemical components such as molecules or ions, to name two.

We use the term "chemical components" broadly to include, for example, chemical compounds, ions, molecules, and other constituents of a sample that may not be present in a form of discernible (e.g., visible) countable units.

We use the term "unit of a chemical component" broadly to include, for example, a single unit of a chemical component such as a single molecule, ion, or other constituent. In typical samples, there are many units of a given type of chemical component, for example, many molecules of a chemical compound.

We use the term "countable units" broadly to include, for example, elements present in a sample that are discrete, discernible, visible, identifiable, and subject to enumeration. Typically, countable units are not transparent. In the case of whole blood, the countable units can include blood cells of different types.

We use the term "chemical analysis" broadly to include, for example, identification and quantification (e.g., determination of the level) of chemical components of one or more types in the sample. In some cases, chemical analysis can include identifying the presence of one or more molecules of one or more types and characterizing the amount, volume, or percentage of each of the types of molecules in the sample or in a particular volume of the sample.

As noted earlier, although the sample analysis technology has a broader range of applications, for convenience we sometimes discuss particular examples in which the sample comprises whole blood or components of whole blood.

We use the term "whole blood" broadly to include, for example, blood in its original form drawn from a human or other animal. Whole blood includes countable units such as blood cells and blood plasma that includes chemical components. As described in the Wikipedia entry titled "Blood plasma" blood plasma is "a yellowish liquid component of blood that normally holds the blood cells in whole blood in suspension. In other words, it is the liquid part of the blood that carries cells and proteins . . . . It is mostly water (up to 95% by volume), and contains dissolved proteins (6-8%) (e.g. serum albumins, globulins, and fibrinogen), glucose, clotting factors, electrolytes ($Na^+$, $Ca^{2+}$, $Mg^{2+}$, $HCO_3^-$, $Cl^-$, etc.), hormones, carbon dioxide (plasma being the main medium for excretory product transportation) and oxygen." Clotting factors include molecules such as plasminogen and prothrombin that participate in clot formation.

We use the term "blood cells" broadly to include, for example, red blood cells (erythrocytes), white blood cells (leukocytes), rare blood cell types, ambiguous blood cell types, and platelets (thrombocytes).

As shown in FIG. 1, typical automated techniques 10 for chemical analysis of blood use fluorescence-based sandwich immunoassay techniques to identify and quantify acellular chemical components 12, for example, molecules of one or more chemical components in blood plasma 14. The "filling" of the "sandwich" in fluorescence-based sandwich immunoassay is, for example, molecules 16 of a given target chemical component in the blood plasma. Each of the molecules is, in effect, sandwiched 18 as a result of adding two types 20, 22 of antibodies to the blood sample. The antibodies of one type 20 are known to bind specifically to one location 24 on the target molecules and serve as "capture antibodies" in the sense that they provide a known "base" at which the target molecules are held. The antibodies of the other type 22 serve as "detection antibodies" and are also known to bind specifically to the target molecules, but to a different location 26 on the target molecules. In some examples, the capture antibodies are fixed, say, to a surface 28 and literally "capture" the target molecules and holds them at a particular location on the surface. The detection antibodies are typically marked by fluorescent molecules 30 attached to them.

Once the target molecules have been captured, that is, bound to the capture antibodies, high intensity excitation light 32 illuminates the sample in one wavelength band causing much lower intensity light to be emitted 34 from the attached fluorescent molecules in a different, typically longer, fluorescence wavelength band. The emitted light is sensed by a light detector 36 (after being passed through a filter 38 to block the much higher intensity excitation light). The light detector is highly sensitive to the presence and intensity level of the relatively low intensity fluorescence wavelength band light and can therefore generate signals indicating the fluorescence intensity and in turn the amount of the target chemical component present in the sample.

The fluorescence sandwich technique can be used to identify and quantify different target chemical components of blood simultaneously by using different appropriate pairs of capture antibodies and suitably labelled (by fluorescent molecules) detection antibodies. In some implementations of such multiplexing, the different capture antibodies are attached at different locations to a fixed surface as a way to differentiate the different target molecules based on their locations at the fixed surface. In some implementations, the target molecules remain dissolved or suspended in the sample and the different capture antibodies are marked using fluorescent beads (for example, Luminex® beads) that produce fluorescence light in different wavelength bands, or different combinations of the bands, as a way to differentiate the different types of target molecules without regard to their locations in the sample.

As discussed later, in some implementations of the sample analysis technology, chemical analysis is combined with a contact monolayer non-fluorescence imaging technique for performing a complete blood count (CBC). For several reasons, the standard fluorescence sandwich technique just described is not optimally compatible with the contact monolayer non-fluorescence CBC technique. One reason is that, in the contact CBC technique, the blood sample is typically in direct contact with a light-sensitive surface of an image sensor which precludes the inclusion of a filter element between the surface and the sample to block the high intensity excitation light. A second reason is that the contact CBC technique is not readily compatible with washing and other processing steps (one of which involves removing non-transparent blood cells from the sample) generally required in fluorescence sandwich immunoassay techniques. The washing and processing steps cannot be easily applied if the same whole blood sample used for the sample analysis technique is to be used also for the contact CBC technique. [Yet, as will be discussed later, because the contact CBC technique is based on the use of a monolayer of blood, portions of the monolayer are free of blood cells and contain only light-passing blood plasma. Therefore, although the entire area of the image sensor may not be suitable for chemical analysis of the target molecules because of the presence of blood cells, some portions of the area of the image sensor are suitable for the sample analysis technique even with whole blood.] A third reason why the fluorescent sandwich technique is not optimally compatible with the contact CBC technique described above is that the small size pixels of the high-resolution image sensor do not provide as adequate low-light sensitivity to detect the low intensity emitted fluorescence light as can a larger-area light detector.

The sample analysis technology that is described here can be used independently to perform chemical analysis of whole blood or can be used to perform chemical analysis of whole blood in combination with or to supplement (simultaneously or sequentially) a contact CBC technique that uses the same sample and light from the same light source. As a result, both the contact CBC technique and the blood chemical analysis can be performed quickly at essentially the same time on a tiny sample of whole blood (for example, a sample of less than 50 microliters or less then 15 microliters or less then 5 microliters) at the point-of-care using a small inexpensive device. Although we often discuss examples in which the chemical analysis is performed on whole blood, the sample analysis technology can be applied to raw whole blood or to whole blood that has been processed to alter or adjust or remove or supplement chemical components or to whole blood from which some or all of the blood cells have been removed, including blood plasma.

We use the term "contact CBC technique" broadly to include, for example, any technique in which blood cells of one or more types are identified and counted in a sample that is in contact with (e.g., within a near-field distance of) a surface of an image sensor. Additional information about contact CBC techniques can be found in one or more of United States patent publications 2016/0041200, 2014/ 0152801, 2018/0284416, 2017/0293133, 2016/0187235, and U.S. Pat. Nos. 9,041,790, 9,720,217, 10,114,203, 9,075, 225, 9,518,920, 9,989,750, 9,910,254, 9,952,417, 10,107, 997, all of which are incorporated here by reference.

Figure 2:
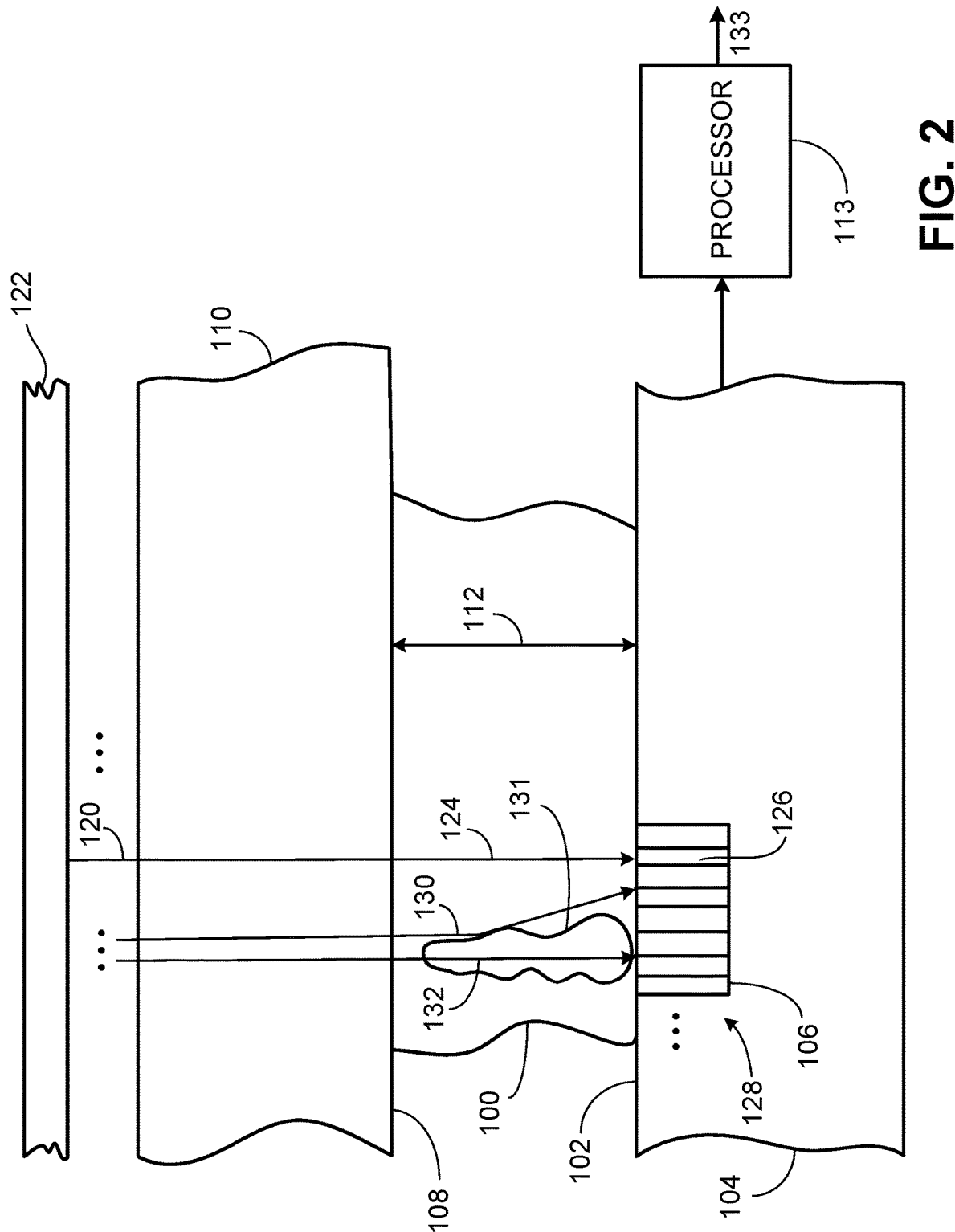
FIG. 2 is a schematic view of chemical analysis of a sample.

Referring to FIG. 2, in some implementations of the sample analysis technology, a monolayer 100 of whole blood is situated between a surface 102 of a high resolution image sensor 104 at which an array of photosensitive elements (e.g., pixels) 106 are exposed and a corresponding surface 108 of a lid 110, to form a monolayer having a known volume defined by its length, width, and thickness 112 between the surface 102 and the surface 108. Examples of structures and techniques for forming such a monolayer are described in one or more of United States patent publications 2016/0041200, 2014/0152801, 2018/0284416, 2017/ 0293133, 2016/0187235, and in U.S. Pat. Nos. 9,041,790, 9,720,217, 10,114,203, 9,075,225, 9,518,920, 9,989,750, 9,910,254, 9,952,417, 10,107,997, all of which are incorporated here by reference.

We use the term "high-resolution" broadly to include, for example, an image sensor that has a pixel spacing in one or both of two dimensions that is smaller than 5 µm, or 3 µm, or 1 µm, or sub-micron, for example.

We use the term "monolayer" broadly to include, for example, a volume of a sample that has a thickness no greater than the thickness of a particular type of unit in the sample, such as blood cells, so that across the monolayer two units cannot be stacked in the dimension defined by the thickness. In the case of a whole blood sample, the thickness of the monolayer could be in the range of 1 micrometer to 100 micrometers.

Light 120 from a light source 122 illuminates the monolayer 100. Portions 124 of the light may pass through the sample monolayer and be received by photosensitive elements 126 in the array 128 of the image sensor. Portions 130 of the light may be reflected or refracted by components 131 of the monolayer and the reflected or refracted light may be received by photosensitive elements in the array. Portions 132 of the light may be transmitted through components of the monolayer and the transmitted light may be received by photosensitive elements in the array; portions of the light may be absorbed by components of the monolayer. As discussed later, the components of the monolayer can include countable units, chemical components, beads, and other elements.

The light source can be configured or controlled or both to provide illuminating light in one or more selected wavelength bands and combinations of them. A wide variety of types of light sources and combinations of them can be used, for example, LEDs, LED panels, organic LEDs, fluorescent panels, incandescent lamps, ambient illumination, arrays of monochrome LEDs, arrays of narrowband sources such as red, green, and blue LEDs or lasers, a miniaturized color display such as a liquid crystal or organic LED (OLED) display or an RGB laser color projector.

Using the light that originates at the light source and passes through, is reflected or refracted by, or is transmitted through the monolayer, the image sensor captures one or more images of the monolayer including countable units of various types (for example, blood cells) and chemical components that are detectable (either in their native condition or as a result of being marked as discussed later). One or more of the captured images are processed by one or more processors or other image processing components 113 to produce information 133 about the whole blood sample including, for example, a CBC or a chemical analysis or both of the countable units and chemical components. Among other things, the resulting information can include a count of red blood cells and their hemoglobin content.

The CBC information can be generated by identifying and counting in the captured images the number of countable units of each type in the sample. Additional information about CBC techniques and about imaging using contact image sensors can be found, for example, in United States patent publications 2016/0041200, 2014/0152801, 2018/0284416, 2017/0293133, 2016/0187235, and in U.S. Pat. Nos. 9,041,790, 9,720,217, 10,114,203, 9,075,225, 9,518,920, 9,989,750, 9,910,254, 9,952,417, 10,107,997, all of which are incorporated here by reference.

Figure 3:
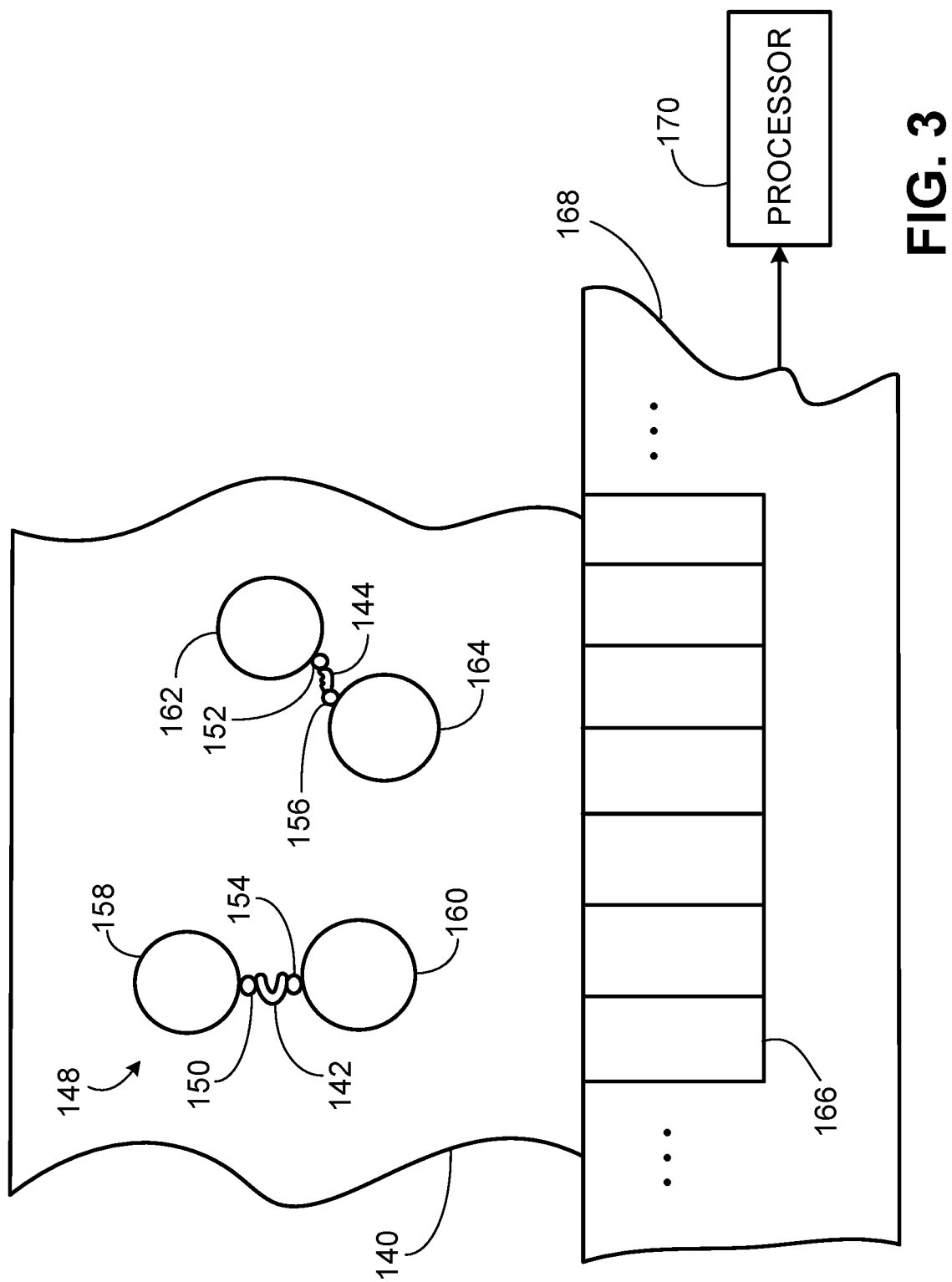
FIG. 3 is a schematic view of chemical analysis of a sample.

As shown in FIG. 3, a monolayer 140 of whole blood (such as the same monolayer of whole blood used for the contact CBC technique) can be used for chemical analysis of various chemical components 142, 144 of the whole blood. For this purpose, individual units of the different types of chemical components of the whole blood monolayer sample can be treated as fillings of sandwiches 148 similar to the fluorescent sandwiches. However, in implementations of the sample analysis technology described here, capture antibodies 150, 152 and detection antibodies 154, 156 are attached to beads 158, 160, 162, 164 that need not have fluorescent properties and are directly visible or otherwise detectable using light that originates at the light source and passes through, is reflected or refracted by, or is transmitted through the monolayer or components of the monolayer. The resulting light is received by light-sensitive elements (e.g., pixel) 166 arrayed in the image sensor 168. (Unlike fluorescence techniques, the light source is not within the monolayer sample but is external to it.)

Using the received light (in some cases, the same received light used for the contact CBC technique), the image sensor captures one or more images of the monolayer sample. One or more processors 170 or other image processing devices process the one or more received images and apply a variety of techniques to identify the presence of and determine the level (e.g., quantity, amount, volume, percentage) of each of the chemical components in the sample.

The beads 158, 160, 160, 162 to which the antibodies 150, 152 and 154, 156 are attached need not have fluorescent properties. The beads can have characteristics that are detectable, visible, or otherwise discernible based on light from the light source that is reflected from, refracted by, or passes through them. We sometimes refer to such beads as "direct indicator beads". The direct indicator beads can take the form of what are sometimes call microbeads in reference to their small size. Microbeads have sizes typically in the range of 0.5 to 500 micrometers.

We use the term "direct indicator beads" (or sometimes simply "beads") broadly to include, for example, any tag, marker, or other indicator device or indicator characteristic that can be attached to or associated with a chemical component of a sample and is identifiable at a sensor using received light that was incident on and reflected or refracted by or transmitted through the indicator device or characteristic. In some cases, direct indicator beads can take the form of small grains, particles, beads, spherules, or other elements, and combinations of them, and can be of a variety of shapes, sizes, materials, and colors.

To determine the presence of units of chemical components in the sample, the processor analyzes the images to detect directly discernible characteristics of beads and complexes of two or more beads that are revealed by light originating from the light source and reflected from, refracted by, or transmitted through the beads to the surface of the image sensor.

We use the term "directly discernible characteristics" of beads and complexes of beads broadly to include, for example, any quality, attribute, or other trait that can be detected, determined, or derived from light that originated at a light source and was reflected from, refracted by, or transmitted through the beads. Directly discernible characteristics could include color, size, texture, birefringence, or shape, or combinations of them, for example.

We use the term "complexes of beads" broadly to include, for example, two or more beads that can be associated with one another because they are attached to a unit in a sample, such as a molecule or other chemical component. Typically, the two or more beads of a complex are detectable in constant close proximity (e.g., touching) one to another. In some cases, the two or more beads of a complex are detectable because they have two or more predetermined different directly discernible characteristics. For example, two beads of a complex may have two specific different colors that are discernible by processing the images from the image sensor.

The sample analysis technology that we describe here can be applied in a variety of different modes.

In some examples of one such mode, which we sometimes call the complexed-beads mode, the chemical components remain dissolved or suspended in the sample. A capture antibody and a detection antibody, each coupled to a separate direct indicator bead, bind simultaneously to the two different locations on a given target molecule or other unit of a target chemical component to form a complex of two beads (i.e., a doublet). [Because each direct indicator bead has more than one of its particular (capture or detection) antibody bound to its surface, a bead may participate in more than one such complex simultaneously, forming a triplet or higher-order bead complex.]

By processing one or more images captured by the image sensor, it is possible to identify those beads present in doublets or higher-order complexes, and thus associated with the chemical component. By determining the proportion of complexed beads to the total number of beads (complexed and singleton, that is, uncomplexed) identified in the sample, it is possible to determine the level or amount or quantity or concentration of the target units (e.g., molecules) of the chemical component in the sample.

It is true that identified singleton beads are not necessarily beads unbound to the target molecule, because in some cases only the capture antibody or the detection antibody, but not both, may have bound to the target molecule.

However, under constant incubation conditions and provided that the concentrations of bead-coupled capture antibodies and bead-coupled detection antibodies in the sample are constant and their ratio is known, it is possible empirically to establish a "standard curve" that represents the relationship between the bead complex index (that is, the proportion of complexed beads to total beads identified by the device) and the concentration of the target molecule.

Figure 4:
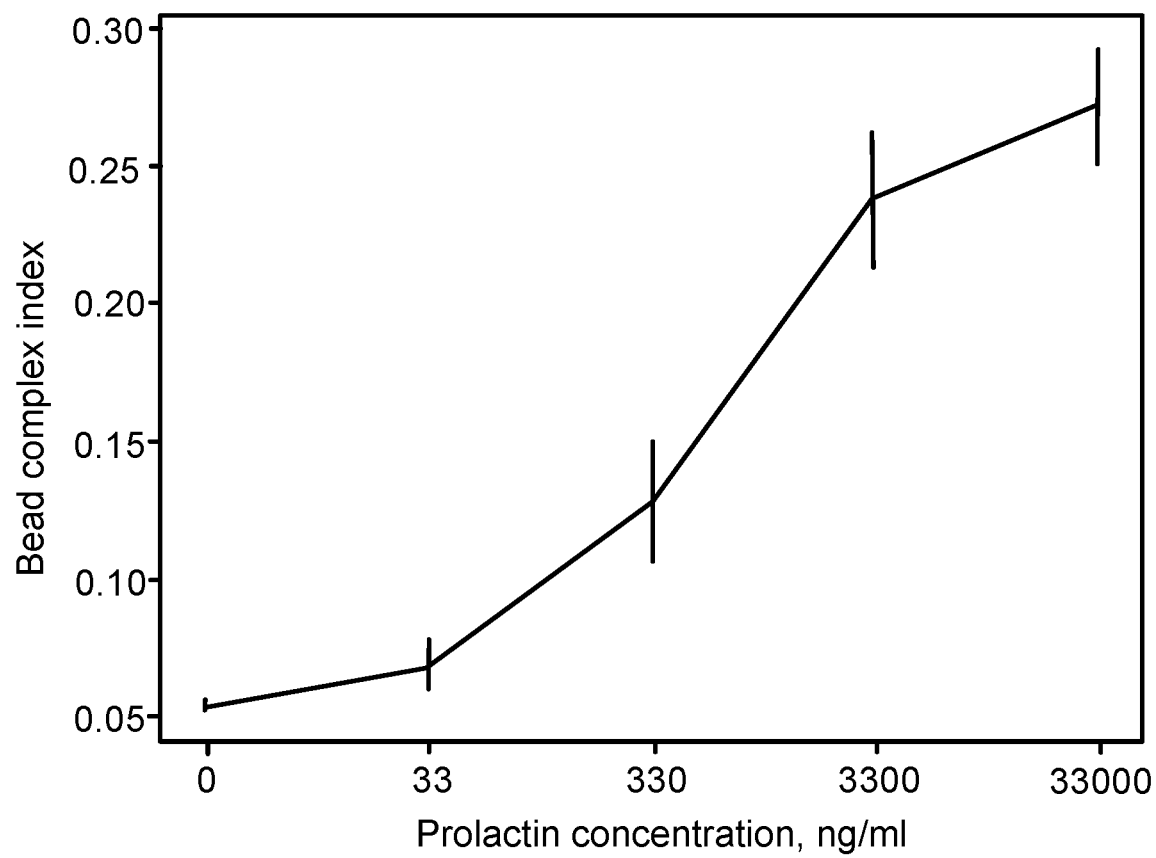
FIG. 4 is a graph of a standard curve.

This has been done experimentally for prolactin to generate the standard curve shown in FIG. 4. Using the standard curve, it is possible to determine the otherwise unknown concentration of prolactin in a sample by determining the bead complex index under identical incubation conditions.

In some implementations, the same beads can be used to mark both the capture antibodies and the detection antibodies that will bind to given units of the chemical component. In some implementations, by using complexes of beads having different directly discernible characteristics for capture antibodies and detection antibodies that are to be attached to the units of different chemical components it is possible to multiplex the process of detecting the presence and levels of the different chemical components at the same time. Multiplexing can be achieved by using beads having different colors, sizes, shapes, textures, or other directly discernible characteristics.

Figure 5:
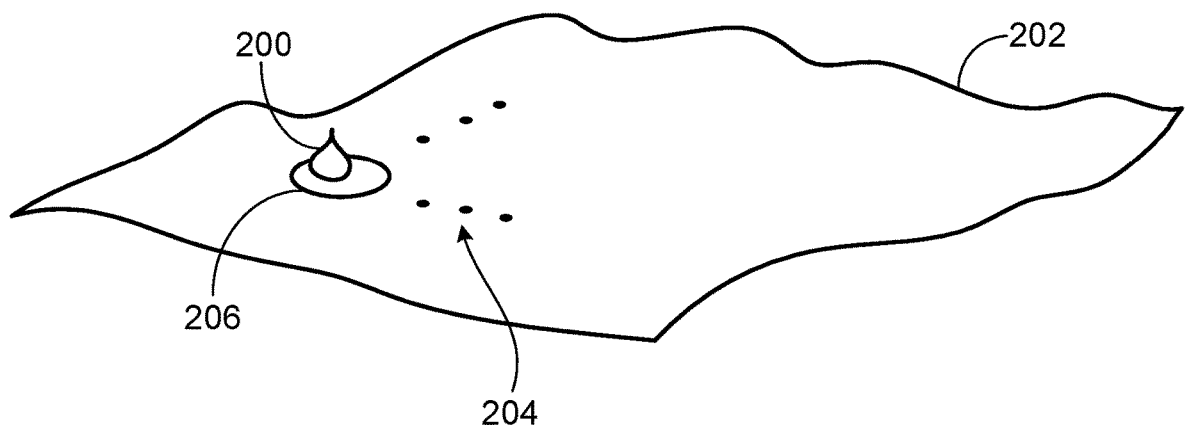
FIG. 5 is a schematic view of a sample.

As shown in FIG. 5, in some implementations, the capture antibodies 200 are irreversibly bound to a fixed surface 202, for example different types of capture antibodies are bound as spots 206 in known corresponding locations in an array 204 on the fixed surface. In such implementations the capture antibodies need not have direct indicator beads attached to them, but the detection antibodies would have direct indicator beads attached to them. The fixed surface could be the surface 108 of the lid 110 that faces the surface 102 of the image sensor 104 and defines a gap occupied by the monolayer 100 of the sample. When the monolayer of the sample is in the gap and in contact with the printed spots in the array of capture antibodies, respective chemical components in the sample will bind to respective capture antibodies, based on the type of the chemical components, in positions defined by the locations of the printed spots in the array, and can at the same time bind to detection antibodies coupled to direct indicator beads. Images captured using incident light that passes through the monolayer and is reflected, refracted or transmitted by the direct indicator beads can then be processed to identify and determine the amounts of different types of chemical components based on the imaged locations of the beads attached to the detection antibodies. This technique of chemical analysis can be used separately or in combination with the contact CBC technique discussed earlier.

In some implementations, a combination of the location-based chemical analysis technique and the in-solution or in-suspension (that is, non-location-based, complexed-beads mode) chemical analysis technique could be used.

In order to use these chemical analysis techniques in combination with the CBC technique in a point-of-care setting, steps must be taken to impart the bead-coupled antibodies to the sample before it is loaded onto the image sensor surface. One approach would be to pass the sample of blood taken from the patient through a tube where dried bead-coupled antibodies are solubilized by the blood and allowed to bind with the target molecules. Then the prepared sample can be placed on the sensor surface. Another approach would be to deposit the bead-coupled antibodies onto the surface 108 of the lid 110 (in some cases in addition to bead-free capture antibodies irreversibly bound at specific locations of the lid) so that they are solubilized when the lid encounters the blood sample in forming the monolayer.

Other implementations are also within the scope of the following claims.

The invention claimed is:
1. A method for identifying a presence or a level of a chemical component in a sample, the method comprising
  binding two or more antibodies to each unit of one or more units of a chemical component in a sample, each of the antibodies also being attached to one or more beads, to form, for each unit of the chemical component, a multi-bead complex of two or more beads, two or more antibodies, and the unit of the chemical component,
  placing the sample on a surface of an image sensor,
  at the image sensor, receiving light originating at a light source, the received light including light reflected by, refracted by, or transmitted through the beads of the multi-bead complexes,
  at the image sensor, capturing one or more images of the sample from the received light,
  enumerating, in at least one of the images of the sample, separate multi-bead complexes, the enumerating of the separate multi-bead complexes comprising associating the two or more beads of the multi-bead complex based on close proximity to one to another, and
  identifying, based on a result of the enumerating, a presence or a level of the chemical component in the sample.
2. The method of claim 1 in which the two or more antibodies bind at different locations of each unit of the chemical component.
3. The method of claim 1 in which the two or more beads of at least a portion of the multi-bead complexes have the same reflective, refractive, and transmissive characteristics.

4. The method of claim 1 in which the two or more beads of at least a portion of the multi-bead complexes have different reflective, refractive, or transmissive characteristics or combinations of them for the light originating at the light source.

5. The method of claim 4 in which the different reflective, refractive, or transmissive characteristics comprise colors of the beads.

6. The method of claim 4 in which the different reflective, refractive, or transmissive characteristics comprise sizes of the beads.

7. The method of claim 4 in which the different reflective, refractive, or transmissive characteristics comprise shapes of the beads.

8. The method of claim 4 in which the different reflective refractive or transmissive characteristics comprise birefringence of the beads.

9. The method of claim 4 in which the different reflective, refractive, or transmissive characteristics comprise textures of the beads.

10. The method of claim 1 in which the placing of the sample on the surface of the image sensor comprises forming a monolayer of the sample on the surface.

11. The method of claim 1 in which the sample comprises whole blood of a human or animal.

12. The method of claim 11, comprising receiving, at the image sensor, light originating at the light source and, in the sample, passing through only blood plasma.

13. The method of claim 1 in which the sample comprises blood cells, the method comprising
  enumerating, in at least one of the images of the sample, blood cells of one or more types in the sample.

14. The method of claim 13 comprising
  determining, based on a result of the enumerating of blood cells of one or more types in the sample, a complete blood count of the sample.

15. The method of claim 1 done at a point-of-care.

16. The method of claim 1, comprising
  causing two or more antibodies to bind to one or more units of a second chemical component in the sample, one or more of the antibodies bound to each unit of the second chemical component being attached to one or more beads, at least another of the antibodies bound to each unit of the second chemical component being attached at a respective known location on a surface,
    wherein the respective known location of each of the antibodies on the surface corresponds to a type of each of the antibodies on the surface,
  identifying, in at least one of the images of the sample, the locations at which the antibodies are attached on the surface having the antibodies attached, and
  based on at least one of the identified locations being a known location corresponding to a type of antibody, determining a presence or a level of the second chemical component in the sample.

17. The method of claim 16 in which the surface to which the antibodies are attached comprises a surface of the image sensor.

18. The method of claim 16 in which the surface to which the antibodies are attached comprises a surface facing the surface of the image sensor.

19. The method of claim 1 comprising passing the sample through a tube before placing the sample on the surface of the image sensor, the tube containing dried antibodies.

20. The method of claim 1 comprising, before placing the sample on the surface of the image sensor, depositing dried antibodies onto the surface of the image sensor.

21. The method of claim 1 in which capturing the one or more images comprises capturing two or more images, and
  in which the received light, for at least two of the two or more images, comprises light of different respective wavelengths.

22. The method of claim 1 comprising enumerating, in at least one of the images of the sample, separate individual beads based on light reflected by, refracted by, or transmitted by each of the separate individual beads and based on a proximity of each of the separate individual beads to other beads.

23. The method of claim 22 in which the identifying comprises determining an amount of the chemical component in the sample based on a comparison of (a) a determined relationship between a number of individual beads and a number of multi-bead complexes and (b) known relationships between the number of the individual beads and the number of multi-bead complexes in other samples having known amounts of the chemical component.

* * * * *

UNITED STATES PATENT AND TRADEMARK OFFICE
CERTIFICATE OF CORRECTION

PATENT NO. : 10,684,278 B1
APPLICATION NO. : 16/368707
DATED : June 16, 2020
INVENTOR(S) : Alan Marc Fine Page 1 of 1

It is certified that error appears in the above-identified patent and that said Letters Patent is hereby corrected as shown below:

In the Claims

Column 11, Line 16-17, in Claim 8, please delete "reflective refractive" and insert -- reflective, refractive, --, therefor.

Signed and Sealed this
Twenty-fifth Day of August, 2020

Andrei Iancu
*Director of the United States Patent and Trademark Office*